United States Patent

Yokoyama et al.

[11] 4,287,362
[45] Sep. 1, 1981

[54] 2-OXOPROPIONALDEHYDE BIS(THIOSEMICARBAZONE) DERIVATIVES

[75] Inventors: Akira Yokoyama, Otsu; Yasushi Arano, Obatamachi, both of Japan

[73] Assignee: Nihon Medi-Physics Co., Ltd., Hyogo, Japan

[21] Appl. No.: 113,341

[22] Filed: Jan. 18, 1980

[30] Foreign Application Priority Data

Aug. 29, 1979 [JP] Japan ................................ 54/110821
Aug. 29, 1979 [JP] Japan ................................ 54/110822

[51] Int. Cl.³ .................. C07C 157/05; C07C 103/52; A61K 43/00
[52] U.S. Cl. ............................ 562/556; 260/112.5 R; 424/1
[58] Field of Search ......................................... 562/556

[56] References Cited

U.S. PATENT DOCUMENTS 3,824,276   7/1974   Murray et al. ........................ 560/251

OTHER PUBLICATIONS

Nishimura, Yakugaku Zasshi, 97, pp. 671–675 (1977).

*Primary Examiner*—Natalie Trousof
*Assistant Examiner*—Michael Shippen
*Attorney, Agent, or Firm*—Birch, Stewart, Kolasch & Birch

[57] ABSTRACT

A radioactive diagnostic agent which comprises a protein and a radioactive metallic element combined with intervention of a bifunctional chelating agent of the formula:

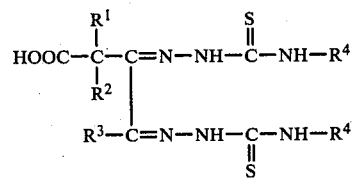

wherein $R^1$, $R^2$, $R^3$ and $R^4$ are each a hydrogen atom or a $C_1$–$C_3$ alkyl group and is characteristic in having high stability even after administered into a human body.

4 Claims, No Drawings

2-OXOPROPIONALDEHYDE BIS(THIOSEMICARBAZONE) DERIVATIVES

The present invention relates to 2-oxopropionaldehyde bis(thiosemicarbazone) derivatives, and their production and use. More particularly, it relates to 2-oxopropionaldehyde bis(thiosemicarbazone) derivatives of the formula:

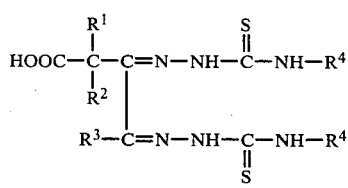

wherein $R^1$, $R^2$, $R^3$ and $R^4$ are each a hydrogen atom or a $C_1-C_3$ alkyl group, their preparation process and their use as a carrier for a radioactive metallic element as well as a protein.

For the purpose of a non-invading nuclear medical diagnosis such as recording, dynamic study and quantitative measurement of a blood circulation system, detection of physiological abnormality or localization of abnormality by imaging, there have been used various proteins labeled with iodine-131 ($^{131}I$) or techentium-99m ($^{99m}Tc$). However, $^{131}I$ has a long half life of about 8 days and emits beta-rays so that the patient administered therewith is exposed to a large quantity of radiation. On the other hand, $^{99m}Tc$ emits gamma-rays of about 140 KeV only and decades with a short half life of about 6 hours. As understood from the above comparison, $^{99m}Tc$ is much more favorable to the use as a labeller for radioactive diagnostic agents than $^{131}I$.

In order to label various proteins with $^{99m}Tc$, there has been generally adopted a process wherein a protein to be labeled is contacted with an aqueous solution containing $^{99m}Tc$ in the form of a pertechnetate in the presence of a reducing agent. However, the thus prepared $^{99m}Tc$-labeled protein is inferior in stability after labeling and also after administration into a human body. When the $^{99m}Tc$-labeled protein is administered into a human body, $^{99m}Tc$ is liberated quickly so that the behavior of the radioactivity does not coincide with the behavior of the $^{99m}Tc$-labeled protein. This is a fatal defect for the nuclear medical diagnosis based on the exact trace of the behavior of the radioactivity which should coincide with the behavior of the labeled protein.

As the result of an extensive study, it has now been found that when a protein is labeled with $^{99m}Tc$ with intervention of the said 2-oxopropionaldehyde bis(thiosemicarbazone) derivative (I), the resulting $^{99m}Tc$-labeled protein is quite stable, particularly in a human body, and can be used as a radioactive diagnostic agent which makes possible highly reliable diagnosis.

The 2-oxopropionaldehyde bis(thiosemicarbazone) derivative (I) is a novel and can be produced by the process as shown below:

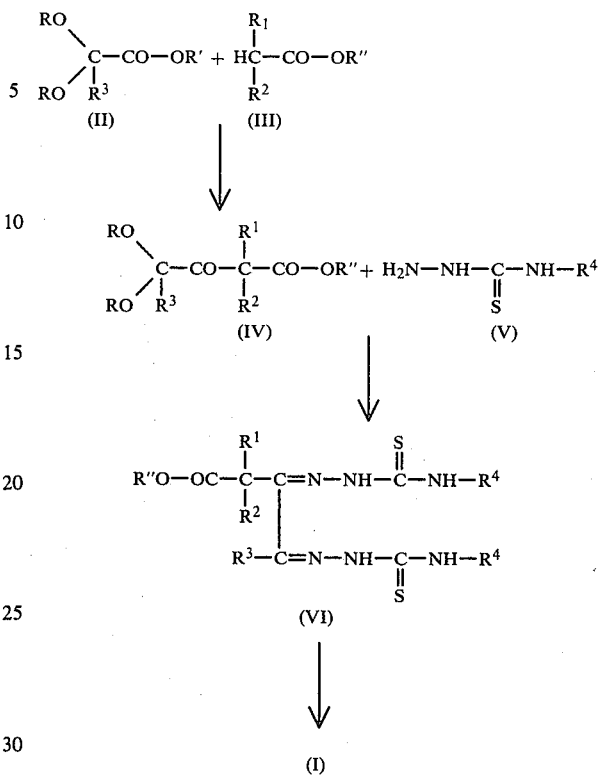

wherein R, R' and R" are each a $C_1-C_5$ alkyl group and $R^1$, $R^2$, $R^3$ and $R^4$ are each as defined above.

Namely, the dialkoxyacetate compound (II) is first condensed with the acetate compound (III). The condensation may be carried out, for instance, in the presence of a condensing agent such as an alkali metal (e.g. sodium) while refluxing. Then, the resulting dialkoxyalkylacetate compound (IV) is condensed with N-alkylthiosemicarbazide (V). The condensation is usually effected in an inert solvent (e.g. methanol, ethanol) at room temperature. The resultant bis(thiosemicarbazone) compound (VI) is then hydrolyzed. The hydrolysis may be accomplished in a per se conventional procedure, for instance, by treating with an acid or an alkali in an aqueous medium.

The thus prepared 2-oxopropionaldehyde bis(thiosemicarbazone) derivative (hereinafter referred to as "OPBT") of the formula (I) has two thiosemicarbazone groups which can catch a radioactive metallic element to form a chelate and a carboxyl group which can be bound with an amino group in a protein and is useful as a carrier for the radioactive metallic element and the protein.

Usually, OPBT (I) is first combined with a protein and then the resultant protein-combined OPBT (I) is labeled with a radioactive metallic element. Examples of the protein are blood proteins (e.g. human serum albumin, fibrinogen), enzyme proteins (e.g. urokinase, streptokinase), hormone proteins (e.g. thyroid stimulating hormone, parathyroid hormone), etc. A typical example of the radioactive metallic element is $^{99m}Tc$.

The combination of OPBT (I) with a protein may be carried out according to any procedure as conventionally adopted for formation of a peptide linkage (—CONH—) in the peptide synthesis. Examples of such procedure are mixed acid anhydride process, acid chloride process, etc. For instance, OPBT (I) is activated at the carboxyl group by the mixed acid anhydride process or the acid chloride process, and the resultant activated OPBT (I) is then reacted with the protein by a per se conventional procedure to give the protein-combined OPBT (I). When desired, this intermediary product may be purified by a per se conventional procedure such as dialysis or gel filtration so as to eliminate impurities such as unreacted reagents therefrom. As the result, the protein-combined OPBT (I) is usually obtained in the form of aqueous solution, and this aqueous solution may be as such used for labeling with the radioactive metallic element. Alternatively, the aqueous solution may be subjected to lyophilization, evaporation under reduced pressure at low temperatures or the like to obtain a dried product, which also can be used as such for labeling. Depending on the use, the said aqueous solution or the said dried product may be incorporated with any additive such as an oxidation inhibitor (e.g. ascorbic acid), an isotonizing agent (e.g. sodium chloride) or a preserving agent (e.g. benzyl alcohol). Still, the protein-combined OPBT (I) is per se quite stable and can be readily labeled with a radioactive metallic element by a simple procedure as hereinafter explained, and therefore it may be stored and supplied on the demand so that its production from OPBT (I) and the protein can be saved for the practitioner such as a medical doctor.

For the labeling of the protein-combined OPBT (I) with a radioactive metallic element, the protein-combined OPBT (I) may be treated with the radioactive metallic element in an appropriate form, usually in an aqueous medium. When, for instance, the radioactive metallic element is $^{99m}$Tc, the protein-combined OPBT (I) may be treated with $^{99m}$Tc in the form of a pertechnetate in an aqueous medium in the presence of a reducing agent such as a stannous salt (e.g. stannous chloride, stannous fluoride, stannous sulfate, stannous nitrate, stannous acetate, stannous citrate). As to the order of the introduction of the above reagents into the reaction system, any particular limitation does not exist. Usually, however, the mixation of the stannous salt with the pertechnetate in an aqueous medium in the first place should be avoided. The stannous salt may be used in such amount as can reduce sufficiently the pertechnetate. The presence of an oxidation inhibitor (e.g. ascorbic acid), an isotonizing agent (e.g. sodium chloride) or the like in the aqueous medium does not materially afford any unfavorable influence on the reduction. No particular limitation is present on the radioactivity of $^{99m}$Tc to be used but it is preferred to be sufficient for obtaining the required information from the patient administered therewith through the nuclear medical diagnosis while suppressing the exposure of the patient to radiation as low as possible. The thus produced radioactive metallic element-labeled, protein-combined OPBT (I) is sufficiently stable, and therefore it may be stored as such and supplied on the demand.

For instance, 3-carboxy-2-oxopropionaldehyde bis(N-methylthiosemicarbazone) (I: $R^1=R^2=R^3=H$; $R^4=CH_3$) (hereinafter referred to as "OPBMT") in the active form on the carboxyl group is treated with human serum albumin, if necessary, followed by elimination of impurities in a per se conventional procedure such as dialysis or gel filtration. The resulting human serum albumin-combined OPBMT is then contacted with $^{99m}$Tc in the form of a pertechnetate in an aqueous medium in the presence of a stannous salt to give the $^{99m}$Tc-labeled, human serum albumin-combined OPBMT, which is highly stable. On the electrophoresis, this product shows the same behavior as that of human serum albumin itself. When administered intravenously to rats, the said product can maintain a much higher blood level for a longer period of time than $^{99m}$Tc-labeled human serum albumin as conventionally produced.

The radioactive metallic element-labeled, protein-combined OPBT (I) of this invention is useful for nuclear medical diagnosis. For instance, $^{99m}$Tc-labeled, human serum albumin-combined OPBMT can be used for recording, dynamic study and quantitative measurement of a blood circulation system by administering intravenously to a human body. Further, for instance, $^{99m}$Tc-labeled, fibrinogen-combined OPBMT or $^{99m}$Tc-labeled, urokinase-combined OPBMT may be used for detection and recording of thrombosis as well as localization of thrombosis, since they accumulate at the locus of thrombosis. Furthermore, for instance, $^{99m}$Tc-labeled, streptokinase-combined OPBMT is useful for determination of the locus of myocardial infarction. Moreover, for instance, $^{99m}$Tc-labeled, thyroid stimulating hormone-combined OPBMT is useful for detection and recording of a cancer at the thyroid gland.

Practical and presently preferred embodiments of the invention are illustratively shown in the following Examples wherein % is by weight, unless otherwise defined.

EXAMPLE 1

Preparation of 3-carboxy-2-oxopropionaldehyde bis(N-methylthiosemicarbazone) (I: $R^1=R^2=R^3=H$; $R^4=CH_3$) (i.e. OPBMT):

(a) To a solution of ethyl diethoxyacetate (24.5 g) in ethyl acetate (12.5 g), metallic sodium (4.2 g) was added, and the resultant mixture was refluxed for about 1.5 hours. The reaction mixture was made acidic with 50% acetic acid and extracted with ether. After removal of the ether from the extract by distillation, the residue was subjected to fractional distillation to give ethyl diethoxyacetoacetate (13.6 g) as a colorless, transparent oil boiling at 84° C./4 mmHg.

(b) To a solution of ethyl diethoxyacetoacetate (4.36 g) in ethanol (40 ml), a solution of N-methylthiosemicarbazide (4.4 g) in N hydrochloric acid (30 ml) was dropwise added. The precipitated crystals were collected by filtration and recrystallized from methanol to give 3-ethoxycarbonyl-2-oxopropionaldehyde bis(N-methylthiosemicarbazone) (6.2 g).

(c) To a solution of 3-ethoxycarbonyl-2-oxopropionaldehyde bis(N-methylthiosemicarbazone (6.2 g) in 1% sodium hydroxide solution (190 ml), 1% hydrochloric acid was dropwise added to make weakly acidic. The produced crystals were collected by filtration and washed with water to give 3-carboxy-2-oxopropionaldehyde bis(N-methylthiosemicarbazone) (4.4 g). M.P., 165°–168° C. (decomp.).

EXAMPLE 2

Preparation of 3-carboxy-2-oxopropionaldehyde bis(N-ethylthiosemicarbazone) (I: $R^1=R^2=R^3=H$; $R^4=C_2H_5$) (hereinafter referred to as "OPBET"):

In the same manner as in Example 1 but using N-ethylthiosemicarbazide in place of N-methylthiosemicarbazide, there was produced 3-carboxy-2-oxopropionaldehyde bis(N-ethylthiosemicarbazone).

EXAMPLE 3

Preparation of 3-carboxy-2-oxobutyraldehyde bis(N-methylthiosemicarbazone) (I: $R^1=R^4=CH_3$; $R^2=R^3=H$) (hereinafter referred to as "OBBMT"):

(a) To a solution of ethyl diethoxyacetate (39.8 g) in ethyl propionate (23.46 g), metallic sodium (4.2 g) was added, and the resultant mixture was refluxed for about 2 hours. The reaction mixture was made acidic with 50% acetic acid and extracted with ether. The extract was subjected to distillation for removal of the ether, whereby ethyl α-(diethoxyacetyl)-propionate (36.8 g) as a colorless, transparent oil.

(b) To a solution of ethyl α-(diethoxyacetyl)propionate (5.08 g) in ethanol (50 ml), a solution of N-methylthiosemicarbazide (5.6 g) in N hydrochloric acid (30 ml) was dropwise added. The precipitated crystals were collected by filtration and recrystallized from methanol to give 3-ethoxycarbonyl-2-oxobutyraldehyde bis(N-methylthiosemicarbazone) (7.8 g).

(c) To a solution of ethoxycarbonyl-2-oxobutyraldehyde bis(N-methylthiosemicarbazone) (7.8 g) in 1% sodium hydroxide solution (200 ml), 1% hydrochloric acid was dropwise added to make weakly acidic. The produced crystals were collected by filtration and washed with water to give 3-carboxy-2-oxobutyraldehyde bis(N-methylthiosemicarbazone (5.2 g).

EXAMPLE 4

Preparation of human serum albumin-combined OPBMT according to mixed acid anhydride process:

Human serum albumin (lyophilized; 1.0 g) was dissolved in a mixture of water (20 ml) and dioxane (5 ml) and adjusted to pH 8 with N sodium hydroxide solution to give a solution (A). Separately, OPBMT (13.2 mg) was dissolved in dry dioxane (1 ml), and tri-n-butylamine (11.6 μl) was added thereto at a temperature below 10° C. After the addition of isobutyl chloroformate (6.4 μl) thereto, the resultant mixture was stirred at a temperature below 10° C. for about 50 minutes to give a solution (B). At a temperature below 10° C., the solutions (A) and (B) were combined together, and stirring was continued at the same temperature as above for about 15 hours.

The resulting mixture was admitted in a dialyzing tube and subjected to dialysis in a conventional manner for 24 hours, followed by lyophilization to give the human serum albumin-combined OPBMT. The above operation were carried out under sterile conditions.

The thus obtained human serum albumin-combined OPBMT was in the form of white cotton crystals. When dissolved in water, it gave a pale yellow, transparent solution.

EXAMPLE 5

Preparation of human serum albumin-combined OPBMT according to mixed acid anhydride process:

An aqueous solution of human serum albumin (25 w/v %; 4.0 ml) was admixed with water (15 ml) and dioxane (5 ml) and adjusted to pH 8 with N sodium hydroxide solution to give a solution (A). Separately, OPBMT (4.5 mg) was dissolved in dry dioxane (1 ml), and triethylamine (2.1 μl) was added thereto at a temperature below 10° C. After the addition of ethyl chloroformate (1.4 μl) thereto, the resultant mixture was stirred at a temperature below 10° C. for about 1 hour to give a solution (B). At a temperature below 10° C., the solutions (A) and (B) were combined together, and stirring was continued at the same temperature as above for about 15 hours.

The resulting mixture was admitted in a dialyzing tube and subjected to dialysis according to a per se conventional procedure for 28 hours. The dyalized solution was diluted with an acetate buffer (pH 5.6) to make a concentration of 10 mg (as human serum albumin)/ml. Gaseous nitrogen was bubbled into the resulting dilution to eliminate the dissolving oxygen therefrom to give an aqueous solution of the human serum albumin-combined OPBMT. An aqueous solution of stannous chloride (0.1 m$\overline{M}$; 10 ml) was added thereto to obtain an aqueous solution of the human serum albumin-combined OPBMT containing stannous chloride. The above operations were effected under sterile conditions.

The said human serum albumin-combined OPBMT solution and the said human serum albumin-combined OPBMT solution containing stannous chloride were almost transparent.

EXAMPLE 6

Preparation of $^{99m}$Tc-labeled, human serum albumin-combined OPBMT:

The human serum albumin-combined OPBMT obtained in Example 4 (75 mg) was dissolved in an acetate buffer (pH 5.6; 1 ml), a physiological saline solution (1 ml) containing $^{99m}$Tc (10.5 mCi) in the form of a pertechnetate was added thereto, and an aqueous solution of stannous chloride (0.1 m$\overline{M}$; 0.1 ml) was incorporated therein to give an aqueous solution containing the $^{99m}$Tc-labeled, human serum albumin-combined OPBMT useful as a radioactive diagnostic agent. This solution was pale yellow, transparent and had around pH 5.

EXAMPLE 7

Preparation of $^{99m}$Tc-labeled, human serum albumin-combined OPBMT:

To the human serum albumin-combined OPBMT solution containing stannous chloride obtained in Example 5 (1 ml), a physiological saline solution (1 ml) containing $^{99m}$Tc (5.8 mCi) in the form of a pertechnetate was added to give an aqueous solution containing the $^{99m}$Tc-labeled, human serum albumin-combined OPBMT useful as a radioactive diagnostic agent. This solution was almost colorless and had around pH 5.

EXAMPLE 8

Properties of $^{99m}$Tc-labeled, human serum albumin-combined OPBMT:

In order to examine the labeling efficiency of the $^{99m}$Tc-labeled, human serum albumin-combined OPBMT obtained in Example 6 or 7, its aqueous solution was subjected to thin layer chromatography using silica gel as a retention material and 85% methanol as a developing solvent, and scanning was carried out by the use of a radiochromatoscanner. In both cases, the radioactivity was recorded as a single peak at the original point. Any peak due to a radioactive impurity such as free pertechnetate ion was not recognized.

Then, the $^{99m}$Tc-labeled, human serum albumin-combined OPBMT obtained in Example 6 or 7 was subjected to electrophoresis (1.6 mA/cm; 90 minutes) using a Veronal-Veronal Na solution (pH 8.6) as a developing solvent and a cellulose acetate membrane as an electrophoretic membrane, and scanning was effected by the use of a radiochromatoscanner. In both cases, the radioactivity was recognized as a single peak at the locus 2 cm distant from the original line to the positive side. This locus was the same as that of the coloring band of human serum albumin with Ponceau 3R.

From the above results, it may be said that the $^{99m}$Tc-labeled, human serum albumin-combined OPBMT obtained in Example 6 or 7 has a labeling efficiency of nearly 100%, and its electric charge is substantially the same as that of human serum albumin.

EXAMPLE 9

Behaviors of $^{99m}$Tc-labeled, human serum albumin-combined OPBMT in rats:

The aqueous solution of the $^{99m}$Tc-labeled, human serum albumin-combined OPBMT prepared in Example 6 or 7 (0.2 ml) was administered intravenously to each of female rats of SD strain, and the variation of the blood level with the lapse of time was recorded. For the control, the same examination as above was carried out by the use of conventional $^{99m}$Tc-labeled, human serum albumin.

The results are shown in Table 1 wherein the blood level at each measuring time is indicated by a relative value (in average) to that immediately after the administration which is taken as 1.0.

TABLE 1

| | Variation of blood level in rats | | | |
|---|---|---|---|---|
| | Time after administration (hours) | | | |
| No. *[1] | 0 | 0.5 | 1 | 2 |
| 1 | 1.0 | 0.97 | 0.95 | 0.90 |
| 2 | 1.0 | 0.98 | 0.94 | 0.91 |
| 3 | 1.0 | 0.73 | 0.58 | 0.45 |

Note:
*[1]No. 1, product in Example 6;
No. 2, product in Example 7;
No. 3, conventional $^{99m}$Tc-labeled human serum albumin.

From the above results, it is understood that the $^{99m}$Tc-labeled, human serum albumin-combined OPBMT of the invention shows a much higher blood level for a longer period of time than conventional $^{99m}$Tc-labeled human serum albumin.

EXAMPLE 10

Stability of human serum albumin-combined OPBMT:

The human serum albumin-combined OPBMT obtained in Example 4 was stored in a refrigerator at 4° to 8° C. for 35 days and then treated with $^{99m}$Tc according to the procedure as in Example 6 to give an aqueous solution containing the $^{99m}$Tc-labeled, human serum albumin-combined OPBMT. With this solution, thin layer chromatography and electrophoresis were carried out according to the procedure as in Example 8 and also behaviors in rats were examined according to the procedure as in Example 9. The obtained results were substantially the same as obtained in Examples 8 and 9. Thus, it may be said that no material change is produced in the human serum albumin-combined OPBMT by the storage for 35 days.

EXAMPLE 11

Stability of $^{99m}$Tc-labeled, human serum albumin-combined OPBMT:

An aqueous solution containing the $^{99m}$Tc-labeled, human serum albumin-combined OPBMT obtained in Example 7 was stored at room temperature (24°–26° C.) for 12 hours. With this solution, thin layer chromatography and electrophoresis were carried out according to the procedure as in Example 8 and also behaviors in rats were examined according to the procedure as in Example 9. The obtained results were substantially the same as obtained in Examples 8 and 9. Thus, it may be said that no material change is produced in the $^{99m}$Tc-labeled, human serum albumin-combined OPBMT by the storage for 12 hours.

What is claimed is:

1. A bifunctional chelating compound of the formula:

$$\text{HOOC}-\underset{\underset{R^2}{|}}{\overset{\overset{R^1}{|}}{C}}-C=N-NH-\overset{\overset{S}{\|}}{C}-NH-R^4$$
$$R^3-C=N-NH-\underset{\underset{S}{\|}}{C}-NH-R^4$$

wherein $R^1$, $R^2$, $R^3$ and $R^4$ are each a hydrogen atom or a $C_1$–$C_3$ alkyl group.

2. The compound according to claim 1, wherein $R^1$, $R^2$ and $R^3$ are each a hydrogen atom and $R^4$ is a methyl group.

3. The compound according to claim 1, wherein $R^1$, $R^2$ and $R^3$ are each a hydrogen atom and $R^4$ is an ethyl group.

4. The compound according to claim 1, wherein $R^1$ and $R^4$ are each a methyl group and $R^2$ and $R^3$ are each a hydrogen atom.

* * * * *